United States Patent [19]

Swain

[11] Patent Number: 4,539,076
[45] Date of Patent: Sep. 3, 1985

[54] VAPOR COMPRESSION DISTILLATION SYSTEM

[76] Inventor: R. L. Bibb Swain, 104 William Claiborne, Williamsburg, Va. 23185

[21] Appl. No.: 424,047

[22] Filed: Sep. 27, 1982

[51] Int. Cl.³ .......................... B01D 3/42; B01D 1/28
[52] U.S. Cl. .................................... 202/154; 202/159; 202/160; 202/161; 202/206; 203/1; 203/2; 203/19; 203/22; 203/23; 203/26; 203/81; 203/DIG. 13
[58] Field of Search ............... 202/159, 153, 154, 160, 202/177, 180, 181, 182, 176, 202, 206, 161; 203/26, 22, 23, 19, DIG. 13, DIG. 14, 1-3, DIG. 25, 74, 81, 98, 99

[56] References Cited

U.S. PATENT DOCUMENTS

| | | | |
|---|---|---|---|
| 2,251,771 | 8/1941 | Wynn et al. | 203/3 |
| 2,352,160 | 7/1944 | Brown | 202/153 X |
| 2,509,136 | 5/1958 | Cornell | 203/26 X |
| 3,029,068 | 4/1962 | Skow | 203/DIG. 17 X |
| 3,293,151 | 12/1966 | Holzer et al. | 202/206 X |
| 3,796,640 | 3/1974 | Boomer | 203/26 X |
| 4,306,940 | 12/1981 | Zenty | 202/83 |
| 4,306,942 | 12/1981 | Brush | 203/23 X |
| 4,329,206 | 5/1982 | Cartland | 202/177 |
| 4,340,446 | 7/1982 | Crawford | 203/26 |
| 4,371,623 | 2/1983 | Taylor | 203/22 |
| 4,372,822 | 2/1983 | Muller et al. | 203/23 X |
| 4,405,409 | 9/1983 | Tusel et al. | 203/19 X |

Primary Examiner—Wilbur Bascomb
Attorney, Agent, or Firm—C. A. Phillips; Michael L. Hoelter

[57] ABSTRACT

A vapor compression distillation system for distillation of any two-component liquid mixture where separation of the more volatile from the less volatile component is required. This system achieves a very high efficiency through the use of vapor compression in conjunction with three heat exchangers: a reboiler which condenses the hot vapors compressed by a vapor pump and uses the heat given up by the condensing vapor to boil bottoms liquid to produce vapor within the stripper, a distillate heat exchanger which recovers heat from the distillate stream, and a bottoms heat exchanger which recovers heat from the outgoing bottoms effluent. This particular component configuration and process results in an exceptionally stable and reliable operation requiring the continuous control of only one parameter, reboiler temperature, while fixing all other process variables. Reboiler temperature is controlled by the use of a heating element which is controlled to give a continuously variable output to assist in preserving stable equilibrium. This close control of the reboiler temperature results in precise control of the operating pressure within the system. This distillation system has several additional features which help its overall energy efficiency and operational stability, including a disengagement section between the reboiler and the stripper, a float chamber to maintain backpressure on the high pressure side of the system, a standpipe assembly for maintaining a liquid filled condition in the bottoms heat exchanger while providing continuous flow for best heat recovery, an optional system for recovery of vapor pump lubricating oil to allow reuse and to prevent fouling of the reboiler heat exchange tubes, and an optional system for cooling the vapor pump by injecting liquid distillate into the pump outlet.

23 Claims, 4 Drawing Figures

VAPOR COMPRESSION DISTILLATION SYSTEM

TECHNICAL FIELD

The present invention relates generally to distillation systems, and more particularly to an alcohol distillation system which is exceptionally energy efficient.

BACKGROUND OF THE INVENTION

Distillation of alcohol and other two-component mixtures has been well known in the past. For centuries, people have been skilled in the art of alcohol distillation. However, many such prior art devices and systems have not been very energy efficient. For example, most distillation systems or stills require the input of energy to produce steam or vapor needed by the process and then later in the system have used cooling water to extract that energy as waste heat.

Some prior art devices use mechanical compression to elevate the condensation temperature of the vapor so that the heat of vaporization can be recovered. Also, some prior art devices have used heat exchangers to extract heat from the distillate as well as from the bottoms. In spite of these improvements in some prior art devices, however, the devices previously known have not taken full advantage of recoverable energy in the effluent streams. Nothing in the prior art has come very close to a 'total heat recovery' design.

An example of a typical prior art distillation system is described in U.S. Pat. No. 1,822,454 to E. Ricard et al. This device appears to be capable of functioning well but does not use vapor compression to recover the heat of vaporization.

A more efficient system is disclosed in U.S. Pat. No. 2,589,406 to A. Latham, Jr. However, Latham's system is suitable only for one-component distillation (i.e., evaporation) since he states that the resistance to internal flow is sufficient to provide the needed backpressure which can be true only for systems where the liquid and vapor have essentially the same boiling/condensation temperature. Also, his system provides no means for enrichment of the vapor in a two-component system. Latham's liquid heat exchanger was not configured to extract maximum energy from the distillate and bottoms, and his on/off control system provided a rollercoaster type of control, making establishment of equilibrium difficult. Latham's device was an efficient one during the World War II era, but it is not sufficient for today's requirements.

Another prior art distillation system is shown in U.S. Pat. No. 3,032,481 to Harding. The Harding device differs from Latham's in that it specifically provides for enrichment of the vapors. However, Harding specifies components such as a steam-heated reboiler and an air-cooled condenser which make his device relatively inefficient.

Therefore, the object of this invention is to develop a system incorporating an improved heat exchanger arrangement which would recover substantially all the heat which is practical to extract from the effluents in the system before they are diverted to storage or disposal. A further object is to incorporate several components and features which would improve the overall efficiency and reliability of the system beyond anything known in the past.

SUMMARY OF THE INVENTION

The present invention is suitable for use in situations where a highly efficient system for separating two-component mixtures of liquids is needed. This system is particularly applicable to the distillation of ethanol, which is used herein as an example. In accordance with the invention, there is provided a distillation system comprising a stripper column, a reboiler unit, a rectifier column, a vapor pump, a distillate heat exchanger, a float chamber, and a bottoms heat exchanger. The stripper column is arranged for the introduction of hot liquid feed into the top and vapor into the bottom, and it has an exit port at its top for escape of low-quality vapor of the lower boiling component. The reboiler unit, which contains liquid, is positioned below the stripper column and comprises heating means for vaporizing the liquid. A vapor line connects the top of the stripper column to the bottom of the rectifier column and carries low-quality vapor from the stripper column to the rectifier column.

The rectifier column, which enriches the vapor to a high degree of purity, is arranged so that its top has a reflux input nozzle and an exit port for the high-quality vapors. The high-quality vapors are carried through a vapor line to the vapor pump where the pressure and temperature of the vapor are increased sufficiently to elevate the condensation temperature of the vapors above the boiling temperature of the liquid in the reboiler. The heated vapor then continues to the reboiler and through the reboiler to an exit at the bottom of the reboiler. The compressed hot vapor gives up its latent heat while passing through the reboiler and in the process condenses to a hot distillate liquid. The heat given up by the condensing vapor passes through the heat exchange tubes in the reboiler and generates vapor on the other side of the tubes by boiling the bottoms liquid. This vapor rises through the stripper column, providing most of the thermal energy needed to make the distillation process function.

After leaving the reboiler, the hot distillate liquid passes through a liquid line to a distillate heat exchanger, which cools the distillate while heating the incoming feed by counterflow heat exchange. The partially cooled distillate then continues to a float chamber which serves several purposes. It first separates the liquid distillate from the non-condensable gases which evolved in the distillation process, metering any excess of distillate above that needed for reflux through the float valve to storage. It next provides a pressurized source of reflux which can either be pumped to the top of the rectifier column or metered through a metering valve by the pressure differential existing between the two points in the system, when that pressure differential is sufficient to provide the force necessary to lift the column of reflux to the top of the rectifier column. Finally, the float chamber contains a backpressure regulator which maintains a prescribed pressure within the system from the float chamber back to the vapor pump, that pressure being sufficient to produce a vapor condensation temperature in excess of the boiling temperature of the liquid bottoms within the reboiler.

A bottoms heat exchanger performs the function of heating the incoming feed liquid while cooling the spent bottoms liquid from which the lower-boiling component has been stripped. The incoming feed is carried by a liquid line from the feed tank through the distillate heat exchanger where it is warmed by recovering heat from the distillate. It then passes through the bottoms heat exchanger where it is further heated by counterflow heat exchange with the bottoms before being introduced into the top of the stripper column. A bottoms liquid line carries spent bottoms from the reboiler and through the bottoms heat exchanger in a counterflow direction to the incoming feed. The spent bottoms continue on to a bottoms pump which pumps the bottoms to a holding tank. Thus, all heat which is practical to recover is removed from the effluents and used in the differential process prior to storage.

DETAILED DESCRIPTION OF THE INVENTION

Figure 1:
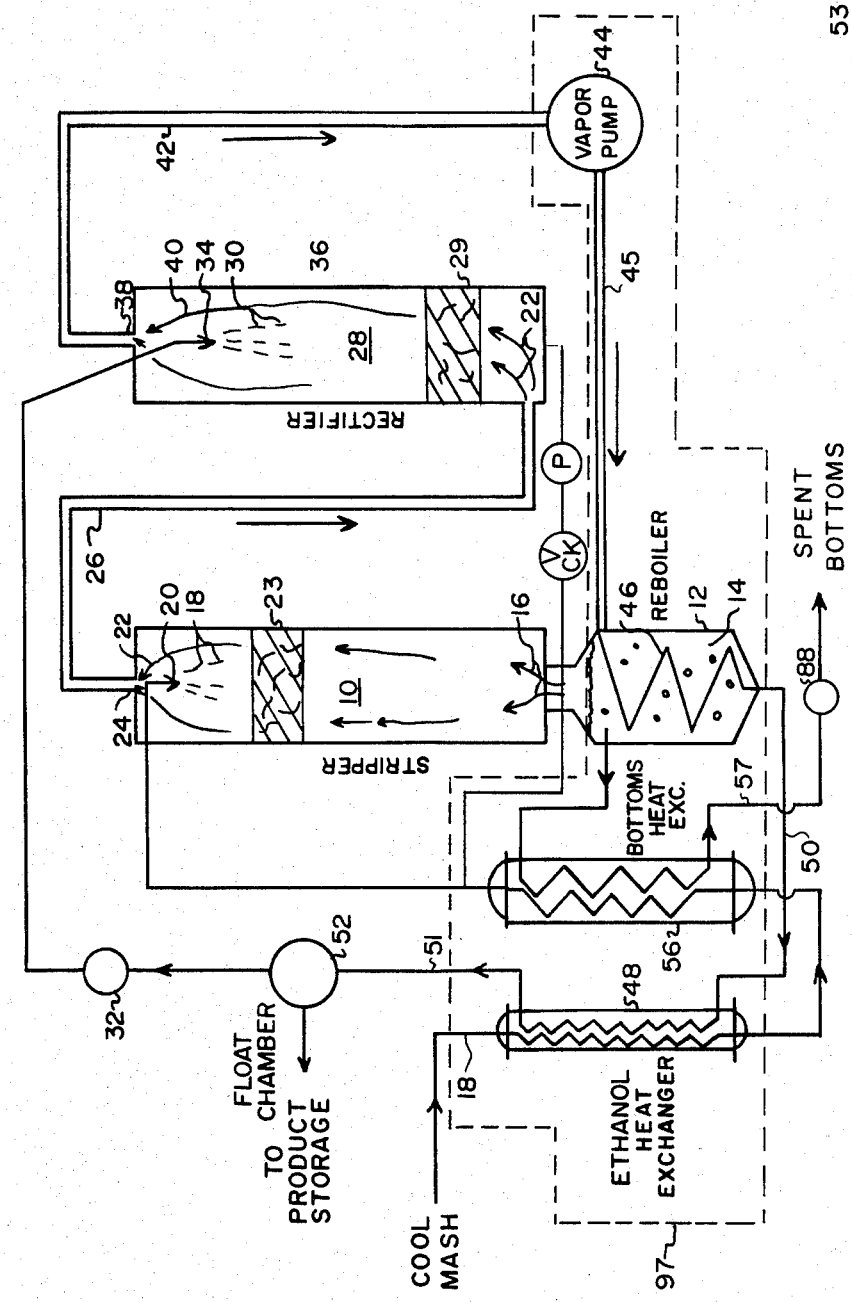
FIG. 1 is a simplified schematic diagram of the invention.

FIG. 1 shows a simplified schematic diagram of the invention. Separation of 10% by weight of ethanol from water at a distillation pressure of 10 PSIA will be used to illustrate the process. In the center of the diagram is shown stripper column 10, where ethanol is stripped from the feed liquid, and reboiler 12, which is the large heat exchanger sitting below stripper column 10. Reboiler 12 contains liquid 14 which is boiling at a temperature of about 193° F. and producing water vapor 16. Vapor 16 rises up through packing material 23 in stripper column 10 at the same time the hot liquid feed 18 is descending. Vapor 16 "strips" the ethanol from feed liquid 18, and the resulting low-proof vapor 22 exits from stripper column 10 through an exit port 24 at the top of column 10. When vapor 22 leaves stripper column 10, it is about 50% ethanol and about 50% water by composition. The temperature at the top of stripper column 10 is about 175° F.

A vapor line 26 conducts the low-proof vapor over to rectifier column 28 where it enters at the bottom and begins to pass up through packing 29 in rectifier 28. At the same time, high-proof liquid alcohol reflux 30 is fed into the top of rectifier 28 through nozzle 34. As low-proof vapor 22 moves up through rectifier column 28, reflux 30 moves down and furnishes the cooling which causes all but 5% to 10% of the water to condense and descend to the bottom of rectifier 28. Rising vapor 22 picks up additional alcohol from vaporized reflux 30 and then passes through exit port 38 at the top of rectifier column 28 as high-proof vapor 40. At this point, the high-proof vapor 40 has experienced a pressure drop of about 1 PSI in passing through packing material 23 and 29 in the two columns and is now at about 9 PSIA. The temperature has dropped to about 151° F., and the vapor composition is about 90% by volume ethanol and 10% water. It should be noted that packing material 23 and 29 substantially fill the stripper column and rectifier column, respectively, although they are shown in both FIGS. 1 and 2 as narrow bands of material, to avoid cluttering the drawings.

Vapor 40 then passes through vapor line 42 from the top of rectifier 28 to vapor pump 44 where the pressure is increased to about 30 PSIA, and the temperature is increased to about 275° F. The hot compressed alcohol vapor 45 now moves from vapor pump 44 to reboiler 12 and passes in contact with heat exchange tubes 46 within reboiler 12 from the top to the bottom of reboiler 12. Vapor 45 gives up its excess sensible heat and all of its latent heat through the walls of heat exchange tubes 46, causing bottoms liquid 14 on the other side of heat exchange tubes 46 to boil and generate steam which rises as vapor 16 through stripper column 10. In the process of giving up its latent heat, hot alcohol vapor 45 in reboiler 12 condenses and passes in liquid form 50 from reboiler 12 to ethanol heat exchanger 48. Hot ethanol liquid 50 moves through ethanol heat exchanger 48 in counterflow direction to incoming mash 18 from the fermenter, giving up heat which is absorbed by the mash 18. Warm alcohol liquid 51 leaves ethanol heat exchanger 48 and moves to float chamber 52 where part of the alcohol is diverted to a product storage tank (not shown), and part is returned to the top of rectifier column 28 as reflux 30.

The incoming mash 18 enters ethanol heat exchanger 48 at about 85° F. and is warmed to about 107° F. in absorbing heat from hot alcohol 50. It then continues into bottoms heat exchanger 56 where its temperature is increased to about 170° F. by absorbing heat from bottoms liquid 14 and on to the top of stripper column 10 via line 80 where it is introduced as hot feed 18. Hot spent mash (bottoms) 14 leaves the reboiler and passes through bottoms heat exchanger 56 in counterflow direction to incoming mash 18, where its temperature is lowered from 193° F. to about 122° F. Spent mash 57 then continues to bottoms pump 88 where it is pumped to a holding tank (not shown) for further processing or direct use as animal feed.

Figure 2:
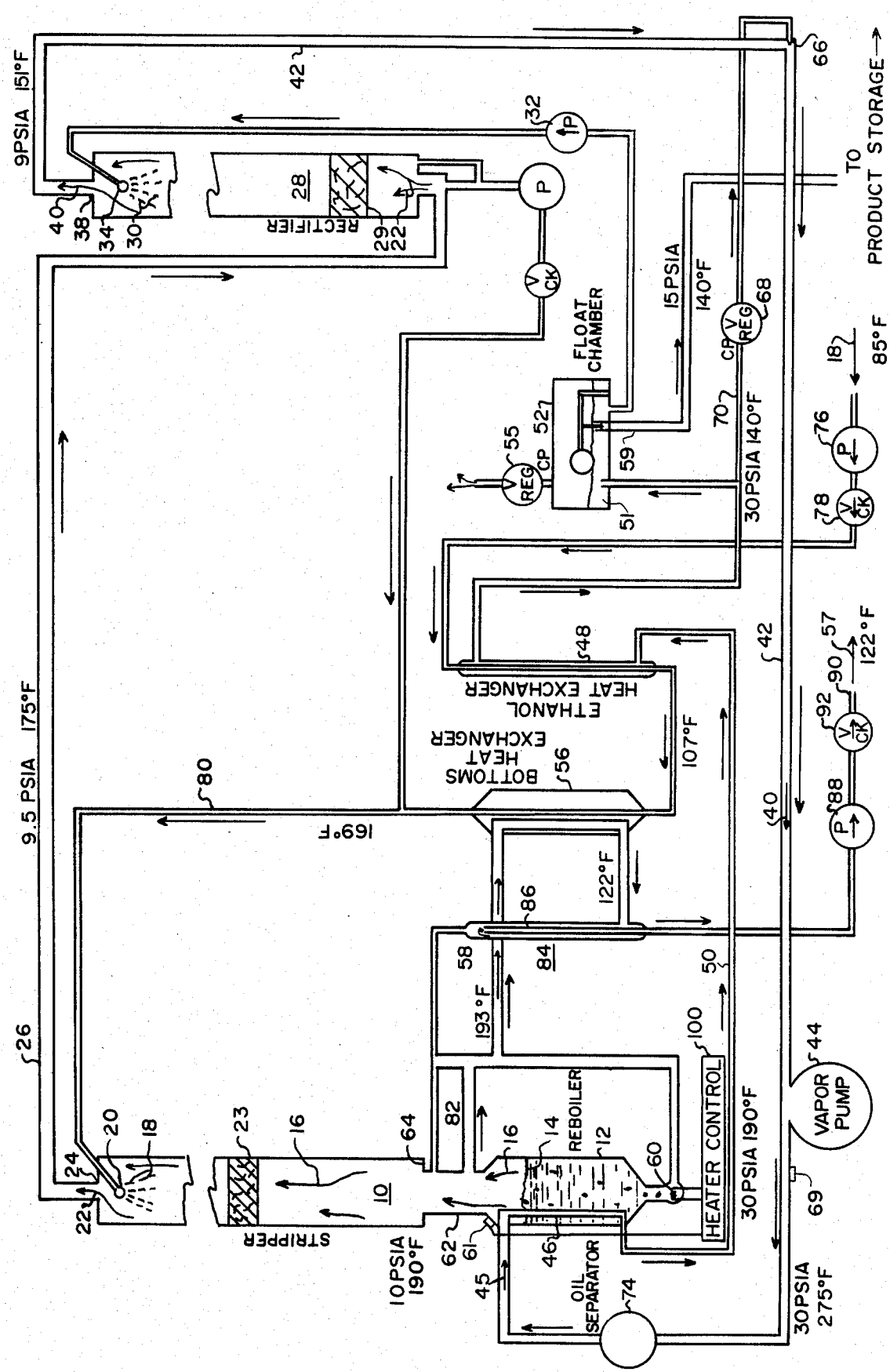
FIG. 2 is a detailed schematic diagram of the invention.

FIG. 2 shows a detailed schematic diagram of a preferred embodiment of the invention. FIG. 2 shows a number of elements and novel features which are not shown in the simplified schematic of FIG. 1.

Looking to the left side of FIG. 2, there is shown stripper column 10 with reboiler 12 sitting beneath it. Reboiler 12 is a heat exchanger which uses the heat from compressed hot alcohol vapor 45 to boil liquid 14 inside reboiler 12 and produce steam (vapor) 16. Electric heating element 60 (any other source of heat can be used where economics provide it more practical) is located in reboiler 12 to preheat the system on start-up and to control the temperature, and thus the pressure, within the low pressure side of the system.

In designing this distillation system, it was found necessary to the proper operation of the system to provide a disengagement section 62 between reboiler 12 and stripper column 10. As liquid 14 boils in reboiler 12, it attains a significant velocity as the bubbles of vapor 16 rise through reboiler 12, causing part of liquid 14 to erupt into bottom 64 of stripper column 10. With the system in full operation, vapor 16 ascending stripper column 10 pushes the excess liquid ahead of it, causing stripper column 10 to "flood," eventually overflowing into rectifier column 28. To prevent this from happening, it was found necessary to provide a sufficient distance between reboiler 12 and stripper column 10 to allow the boiling liquid 14 to disengage from vapor 16 and fall back into reboiler 12 instead of entering base 64 of stripper column 10.

When the fermented mash (or beer) 18 is introduced into the top of stripper column 10, vapor 16 rising from reboiler 12 strips the alcohol from mash 18 by vaporizing it. Using the previously stated example, low-proof vapor 22 leaves stripper column 10 at a pressure of about 9.5 PSIA, a temperature of about 175 F., and a composition of about 50% ethanol and 50% water.

Low-proof vapor 22 enters the bottom of rectifier column 28 and passes up through packing 29 in the rectifier. At the same time, liquid alcohol reflux 30 is being fed into the top of rectifier 28 from float chamber 52. Reflux 30, which is about 90% by volume ethanol, cools the vapor as it rises through the rectifier. This cooling action preferentially condenses the water from low-proof vapor 22, removing all but about 10% by volume of the water. At the same time the water is condensing, liquid alcohol reflux 30 is vaporizing. Therefore, high-proof vapor 40 leaving rectifier 28 consists of the alcohol which freshly entered rectifier 28 from stripper column 10 as well as most of the alcohol which was recycled into the rectifier as reflux 30, plus a portion of water from both sources. At this point, the vapor 40 composition is about 90% ethanol, with a pressure of about 9 PSIA, and a temperature of about 151° F. High-proof vapor 40 now passes through vapor line 42 to the inlet of vapor pump 44.

Intermediate between rectifier 28 and vapor pump 44 is nozzle 66 connected through metering valve 68 to liquid alcohol source 70 for injecting liquid alcohol into vapor pump inlet 42. This arrangement provides internal cooling for vapor pump 44 by allowing the liquid alcohol to absorb heat from the hot internals of pump 44 while itself vaporizing. The advantage of this arrangement is that cooling so provided is available for recovery in reboiler 12 instead of being discarded as waste heat if provided by conventional external means. Temperature sensing unit 69 at the outlet of vapor pump 44 can be used to automatically control the quantity of alcohol injected, or a manual metering valve can be used. It should be noted that a cooling system for the vapor pump is needed if the particular pump selected is incapable of operating reliably at the temperatures encountered by an uncooled system. Its use allows the operator of the system to select a very low inlet operating pressure, if desired.

The purpose of vapor pump 44 is to increase the pressure of alcohol vapor 40 sufficiently to elevate its condensation temperature above the boiling temperature of the liquid bottoms within reboiler 12. A practical pressure ratio for an ethanol/water system has been found to be about 3:1 between the vapor and liquid pressures, respectively, within reboiler 12. The lower the ratio, the larger the reboiler transfer surface area must be to transfer the heat from the vapor to the liquid. The higher the ratio, the more energy is required to drive vapor pump 44. Therefore, for an ethanol/water system, the vapor exits the vapor pump at a pressure of about 30 PSIA. On compression, the vapor heats up to about 275° F. This is due to a combination of the heat of compression plus the heat produced by friction within the pump. The actual temperature attained will thus depend on pump efficiency as well as several other factors.

If vapor pump 44 selected is a type which allows lubricating oil to enter the vapor stream, hot compressed vapor 45 next enters oil separator 74 where the oil is removed from vapor 45 to prevent fouling of reboiler 12 and for possible reuse. Oil separator 74 is a commercially available unit, and while it is considered necessary to the best efficiency of the invention, it is not considered novel per se. Vapor pump types which produce an oilless exhaust will need no oil separator.

Next, hot vapor 45 enters the reboiler where it gives up heat through the walls of heat exchange tubes 46, condensing to a liquid 50 in the process. The heat given up by alcohol vapor 45 boils the liquid bottoms 14 within reboiler 12, producing steam (vapor) 16 which rises into stripper column 10 after leaving reboiler 12. Hot liquid alcohol 50 passes into ethanol heat exchanger 48 where it gives up heat and warms incoming mash 18 from the fermenter.

When the alcohol leaves the ethanol heat exchanger, it passes to float chamber 52, which will be described in detail in connection with FIG. 3.

A portion of alcohol 51 is diverted to product storage while the remainder is sent to the top of the rectifier as reflux 30. Reflux 30 can be delivered to the top of rectifier 28 in either of two ways. If the operating pressure selected is such that a sufficient pressure differential exists between float chamber 52 and the top of rectifier 28 to force reflux 30 to flow without need of a pump, then a simple metering valve 98 (FIG. 4) is all that is needed to regulate the flow of reflux 30 to provide the prescribed amount to the top of rectifier 28. Otherwise, pump 32 must be provided in the line between float chamber 52 and the top of rectifier 28 to pump reflux 30 to the top of rectifier 28.

Now, the path of feed 18 through the system will be traced. Incoming mash 18 from the fermenter (not shown) enters the system at about 85° F. In our example, it contains about 10% ethanol by weight. Positive displacement pump 76 meters feed 18 into the system at a prescribed rate. Since the system may be operating at a vacuum, a backpressure regulator 78 is located just downstream of feed pump 76 to prevent the vacuum from pulling more feed into the system than desired. The backpressure provided by backpressure regulator 78 is sufficient to offset the system vacuum, thereby permitting pump speed to regulate feed rate rather than allowing vacuum to regulate feed rate. After feed 18 leaves pump 76 and backpressure regulator 78, it enters ethanol heat exchanger 48 where it absorbs heat from the alcohol that is being cooled, increasing its temperature to about 107° F.

Next, warm feed 18 enters bottoms heat exchanger 56. Here, the primary purpose is to recover the maximum amount of heat that is practical from the hot spent mash which is leaving the system. The mash enters bottoms heat exchanger 56 at about 107° F. and leaves at about 169° F. The hot mash now ascends via line 80 to the top of stripper column 10 where it is injected into column 10 through nozzle 20. Liquid mash (feed) 18 gradually descends through packing 23 in stripper column 10 where the alcohol is stripped (vaporized) from it by the hotter vapor 16 that is rising out of reboiler 12. When the feed reaches bottom 64 of stripper 10, there is little alcohol remaining in it. For economical operation, mash 18 should contain no more than one-tenth of 1% of ethanol when it reaches the bottom of stripper 10 as spent mash 14. At that point, spent mash 14 consists primarily of water plus dissolved solids and particles which come from the corn or other fermented organic material.

When liquid 14 reaches the reboiler, part of it is boiled back up to produce steam 16 required to make the system operate. More of the hot spent bottoms 14 will overflow into overflow line 82 and on into the inlet of the bottoms heat exchanger 56. Bottoms 14 enter bottoms heat exchanger 56 at a temperature of about 193° F., pass through in a counterflow direction to incoming mash 18 and exit at about 122° F. From there, bottoms 57 enter a standpipe system 84 which has the purposes of maintaining a liquid-filled condition within heat exchanger 56 and permitting continuous flow of bottoms 57 without exotic control mechanisms, both conditions tending to increase system reliability and efficiency while decreasing complexity. As bottoms 57 overflows through central pipe 86 in standpipe system 84, it is conducted through pump 88 which pumps it through check valve 92 and on to storage. Pump 88 is set to operate at a slightly higher rate than the flow rate of liquid bottoms 57 so that total evacuation of the system will be assured. Check valve 92 prevents backflow into the system during start-up or during troubleshooting when pump 88 may not be in operation.

Figure 3:
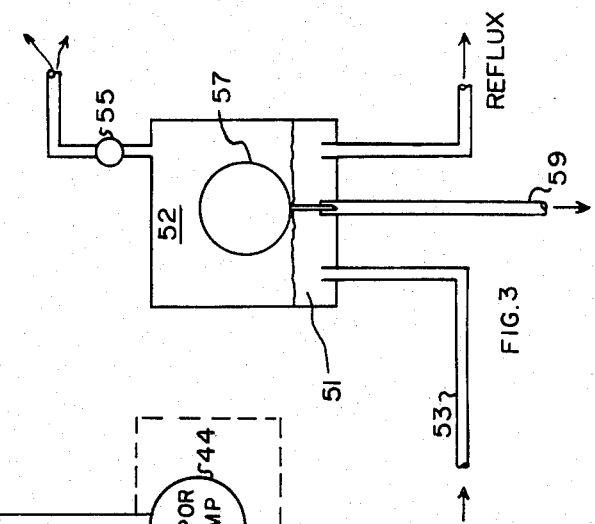
FIG. 3 is a side view showing the design of the float chamber.

Looking now to FIG. 3, there is shown the design of float chamber 52. Inlet 53 of float chamber 52 brings in liquid alcohol 51 plus any non-condensable gases which may have leaked into the system or evolved from the feed being distilled.

Figure 4:
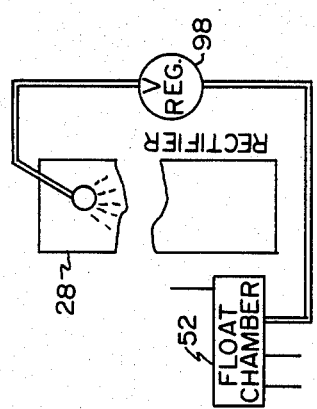
FIG. 4 is a detailed schematic view, partially broken away, of an alternate flow control between the float chamber and the rectifier.

At the top of float chamber 52 is a backpressure regulator 55 which impedes any non-condensable gases from leaving the chamber. It holds a constant pressure within chamber 52 by releasing only enough gas to offset the amount entering chamber 52. By controlling the pressure within chamber 52, the pressure is controlled throughout the system back through vapor pump 44 outlet. This is a critical parameter because it is this pressure which determines the condensation temperature of alcohol vapor 45 within the reboiler. As more liquid alcohol accumulates in chamber 52, the float rises slightly to allow a larger quantity to leak through outlet liquid line 59 and proceed on to a storage tank (not shown) as product. Reflux 30 leaves chamber 52 through outlet to either reflux pump 32 or to a metering valve 98 (FIG. 4).

Control element (heater) 60 is located at the bottom of reboiler 12. Sensing device 61, which controls heater 60, is located in the top of reboiler 12 above the level of liquid 14. The heater control system 100 comprising heater 60 and sensing device 61 performs the valuable function of establishing and maintaining the desired temperature within the reboiler. By controlling the temperature within a closed boiling system, one also controls the pressure. If a given amount of liquid at its boiling point is exposed to a lower pressure, it responds by boiling up more vapor to attempt to restore the original pressure. Therefore, if the temperature is maintained steady in a boiling system with continuous evacuation of the vapors, the pressure within the system will also remain constant at the vapor pressure of the boiling liquid. It is possible to insulate the system so well and otherwise recover enough energy from the effluent streams that the excess energy input through vapor pump inefficiency causes the temperature within the system to gradually increase until some higher than desired equilibrium temperature is reached. To prevent the temperature and pressure from so drifting, this invention intentionally allows enough heat to escape the system so that use of control element 60 will be required, thereby permitting a control sensor and element 60 to establish the desired system pressure. Control element 60 is the only unit in the system which is controlled on a continuous basis. Other possible variables in the system are preset and are adjusted only occasionally. For example, the feed rate and reflux rate are both initially adjusted to the desired system performance and then left constant. If the alcohol content in the feed changes, a different reflux ratio is required to maintain the same product quality (proof). If the feed quality decreases, a higher reflux ratio (reflux divided by product rate) is required. By maintaining a constant rate of feed and reflux, as the product rate decreases due to a lesser amount of alcohol entering the system, the reflux ratio is changed by almost the exact right amount to hold the product quality constant. Therefore, by merely controlling the temperature in the reboiler, the entire system is held in a very stable equilibrium. The extreme simplicity of the control system is considered a novel feature of this invention.

The alcohol distillation system described above is highly efficient. A number of earlier systems required a great deal of energy input into the reboiler or into the base of the stripper to furnish the vapor necessary to strip the alcohol from the feed. The present system recovers a maximum practical amount of heat from all effluent streams through the use of all three of the following heat exchangers. First, the reboiler recovers latent heat from the alcohol vapor to boil the liquid which generates the steam needed in the stripper. Second, the ethanol heat exchanger recovers sensible heat from the alcohol to warm the feed. Third, the bottoms heat exchanger recovers heat from the bottoms to further warm the feed.

In the present invention, utilizing it as an ethanol/water system, the concentrated vapors have a condensation temperature of about 151° F., whereas the temperature of about 193° F. was required to create the initial vapor. Under previously known processes, that heat could not be fully recovered. Condensation would normally be accomplished with cooling water, thereby dissipating the latent energy of the vapor as waste heat. However, excepting for conductive heat losses in the columns, the final vapor will give up the same amount of heat on condensation that was required to boil up the original vapor in the reboiler although at too low a temperature to be usable for such. In the present invention, since condensation temperature is a function of pressure, the vapor pump compresses the vapor to a pressure high enough to elevate the condensation temperature above the boiling temperature of the liquid in the reboiler. Therefore, all latent heat in the vapor can be recovered, virtually recycling it back into the front end of the process. The price paid for the recovery is the mechanical energy needed to compress the vapors, which is only a fraction of the energy recovered.

An additional feature of this invention that makes the system more efficient is that all components which operate at an elevated temperature are placed in an insulated enclosure 97 to reduce heat loss to the atmosphere and to simplify construction.

Described above is a distillation system which combines a number of features which provide greater overall efficiency than any system known before. The system utilizes a combination of three heat exchangers which extract all the available heat that is practical to extract from the effluents before they are sent to storage. Other features of the invention which contribute to its high overall efficiency, ease of construction, and stability and reliability of operation are:

(1) a disengagement section between the reboiler and the stripper column to prevent flooding of the stripper column;

(2) a positive displacement pump and backpressure valve in the feed line to meter feed liquid into the system;

(3) a float chamber containing mechanisms to provide the desired backpressure on the system back to the vapor pump, to divert the proper amount of distillate to product storage, and to provide a pressurized source of reflux liquid;

(4) a standpipe assembly in the line between the bottoms heat exchanger and the bottoms pump to increase heat transfer efficiency by maintaining the bottoms heat exchanger full of liquid in a fail-proof manner;

(5) a positive displacement pump operating at a fixed pumping rate slightly higher than needed in conjunction with the standpipe assembly to provide continuous flow of liquid through the bottoms heat exchanger and positive evacuation of the bottoms from the system.

(6) an insulated enclosure 97 which contains all components which operate at an elevated temperature to reduce heat losses;

(7) an optional oil separator to recover the oil used to lubricate the vapor pump; and (8) an optional nozzle and metering valve at the inlet of the vapor pump to inject liquid distillate into the pump inlet for pump cooling when needed.

What is claimed is:

1. A distillation system comprising:
 a stripper solumn arranged for the introduction of hot feed liquid into the top and vapor into the bottom, said stripper column having an outlet means at its top for eszcape of exiting vapors and an inlet means at its bottom for the entrance of said vapor;
 a reboiler unit positioned below said stripper column and coupled to said inlet means, said reboiler containing liquid and comprising heating means for producing vapor from said liquid;
 a rectifier column for enriching the vapor which exited the stripper column, the bottom of said rectifier column comprising inlet means for said vapor, and the top of said rectifier column comprising means for outlet of the enriched vapor and inlet of liquid reflux;
 a first line for transmitting vapor from the top of the stripper column to the bottom of the rectifier column;
 a vapor pump for increasing the pressure and temperature on said enriched vapor;
 a second line for transmitting said enriched vapor from the top of said rectifier column to said vapor pump;
 a third line for transmitting said hot compressed enriched vapor from said vapor pump to the top of said reboiler and continuing through said reboiler to an exit at the bottom of said reboiler;
 a distillate heat exchanger for cooling the distillate liquid and heating the incoming feed liquid;
 a fourth line in continuation of said third line connecting the bottom of said reboiler with said distillte heat exchanger in counterflow direction to said incoming liquid feed;
 a float chamber to amintain the desired backpressure on the system back to said vapor pump, to divert the proper amount of distillate to storage, and to provide a pressureized source of relux liquid;
 a fifth line for conduting liquid distillate from said distillate heat exchanger to said float chamber;
 a sixth line for carrying a portion of said distillate as reflux from said float chamber to the top os adi rectifier column;
 a bottoms heat exchanger;
 a seventh line for bringing incoming cool feed liquid into the system through said distillate heat exchanger continuing through said bottoms heat exchanger and connecting to the top of said stripper column for warming feed liquid in said distillate heat echanger, further heating said feed liquid in said bottoms heat exchange, and introducing said hot liquid feed into the top of said stripper column;
 an eighth line for carrying hot spent liquid bottoms from said reboiler to said bottoms heat exchanger, continuing through said bottom sheat exchanger in counterflow direction to said seventh liquid line, and continuing through a bottoms outlet pump; and
 a ninth line connected to said float chamber for conducting distillate product from said float chamber to product storage;
 whereby available heat from said bottoms liquid and said distillate vapor is withdrawn and reused by the distillation unti before said bottoms liquid and said distillate product exit the system to storage.

2. the distillation system of claim 1 comprising a positive displacement pump operating at a fixed rate to meter said incoming feed liquid into the distillation system.

3. The distillation system of claim 2 comprising a backpressure valve at the outlet of said positive displacement pump to provide an outlet pressure higher than the inlet pressure.

4. The distillation system of claim 1 comprising a disengagement section between said reboiler and said stripper column to prevent flooding of said stripper column.

5. The distillation system of claim 1 comprising a standpipe assembly in said eighth liquid line between said bottoms heat exchanger and said bottoms outlet pump to maintain a liquid filled condition in said bottoms heat exchanger.

6. The distillation system of claim 5 wherein said bottoms outlet pump is downstream from said standpipe assembly and said system further comprising a check valve downstream of said pump, said pump and valve evacuating said liquid bottoms from said reboiler and preventing backflow during unusual operating conditions.

7. The distillation system of claim 1 comprising an insulated enclosure wherein all components of said distillation which operate at an elevated temperature are located, and all equipment which operates at ambient temperature or requires cooling are outside said insulated enclosure in a separate equipment area.

8. The distillation system of claim 1 comprising a sensing means to detect the temperature in said reboiler and a control means connected to said heating means in said reboiler unit and to said sensing means to control the temperature of the boiling liquid in said reboiler and provide preheating for initial start-up.

9. The distillation system of claim 1 comprising an oil separator in said third line for recovering oil introduced into said third line by oil lubrication of said vapor pump.

10. the distillation system of claim 1 comprising a positive displacement liquid pump coupled to said sixth line for metering reflux into the top of said rectifier column.

11. The distillation system fo claim 1 comprising a metering valve coupled to said sixth line to control the flow rate of said reflux and utilizing the pressure differential existing between said float chamber and said rectifier column to provide the pumping force for said reflux.

12. The distillation system of claim 1 comprising a nozzle in said second line connected through a metering valve to said fifth line in order to introduce liquid distillate into the inlet of said vapor pump to provide internal cooling for said vapor pump in a manner which allows the cooling energy to be recovered.

13. The distillation system of claim 12 comprising a temperature sensing unit, at the outlet of said vapor pump for use in automatically controlling said metering valve to continuously control the operating temperature of said vapor pump.

14. The distillation system of claim 3 comprising a sensing means to detect the temperature in said reboiler and a control means connected to said heating means in said reboiler and to said sensing means to control the temperature of the boiling liquid in said reboiler and provide preheating for initial start-up.

15. The distillation system of claim 14 comprising a positive displacement liquid pump coupled to said sixth line for metering reflux into the top of said rectifier column.

16. The distillation system of claim 14 comprising a metering valve coupled to said sixth line to control the flow rate of said reflux and utilizing the pressure differential existing between said float chamber and said rectifier column to provide the pumping force for said reflux.

17. The distillation system of claim 15 comprising a disengagement section between said reboiler and said stripper column to prevent flooding of said stripper column.

18. The distillation system of claim 17 comprising a standpipe assembly in said eighth liquid line between said bottoms heat exchanger and said bottoms outlet pump to maintain a liquid filled condition in said bottoms heat exchanger.

19. the distillation system of claim 18 wherein said bottoms outlet pump is a positive displacement pump positioned downstream from said standpipe assembly, and said system further comprises a check valve downstream of said pump, said pump and valve evacuating liquid bottoms from said reboiler and preventing backflow during ususual operating conditions.

20. The distillation system of claim 19 comprising a nozzle in said second line connected through a metering valve to said fifth line in order to introduce liquid distillate into the inlet of said vapor pump to provide internal cooling for said vapor pump in a manner which allows the cooling energy to be recovered.

21. The distillation system of claim 20 comprising a temperature sensing unit at the outlet of said vapor pump use in for automatically controlling said metering valve to continuously control the operating temperature of said vapor pump.

22. The distillation system of claim 21 comprising an oil separator in said third line for recovering oil introduced into said third line by oil lubrication of said vapor pump.

23. The distillation system of claim 22 comprising an insulated enclosure wherein all components of said distillation which operate at an elevated temperature are located, and all equipment which operates at ambient temperature or requires cooling are outside said insulated enclosure in a separate equipment area.

* * * * *